United States Patent [19]

Purdy et al.

[11] Patent Number: 5,360,004
[45] Date of Patent: Nov. 1, 1994

[54] NON-INVASIVE DETERMINATION OF ANALYTE CONCENTRATION USING NON-CONTINUOUS RADIATION

[75] Inventors: David L. Purdy, Marion Center; Richard L. Wiggins; Paul Castro, both of Indiana, all of Pa.

[73] Assignee: Diasense, Inc., Pittsburgh, Pa.

[21] Appl. No.: 59,164

[22] Filed: May 7, 1993

Related U.S. Application Data

[63] Continuation-in-part of Ser. No. 987,766, Dec. 9, 1992.

[51] Int. Cl.$^5$ .............................................. A61B 5/00
[52] U.S. Cl. ................................... 128/633; 128/664; 356/39
[58] Field of Search ........................... 128/633–634, 128/664–667; 356/39–41

[56] References Cited

U.S. PATENT DOCUMENTS

| | | | |
|---|---|---|---|
| 3,463,142 | 8/1969 | Harte | 128/633 |
| 4,655,225 | 4/1987 | Dahne et al. | 128/664 X |
| 4,882,492 | 11/1989 | Schlager | 128/633 X |
| 5,070,874 | 12/1991 | Barnes et al. | 128/633 |

*Primary Examiner*—Angela D. Sykes
*Attorney, Agent, or Firm*—William H. Murray; Robert E. Rosenthal; Steve Mendelsohn

[57] ABSTRACT

A method and apparatus for non-invasive determination of the concentration of at least one analyte in a mammal. A portion of the body of the mammal is irradiated with incident radiation, where the incident radiation includes two or more distinct bands of continuous-wavelength incident radiation. The resulting radiation emitted from the portion of the body is sensed and a value for the concentration of the analyte is derived therefrom.

20 Claims, 5 Drawing Sheets

NON-INVASIVE DETERMINATION OF ANALYTE CONCENTRATION USING NON-CONTINUOUS RADIATION

BACKGROUND OF THE INVENTION

This application is a continuation-in-part of copending application Ser. No. 07/987,766, filed Dec. 9, 1992, pending.

This invention relates to techniques for non-invasively detecting the concentration of analytes in living animals, and in particular to the use of infrared and near-infrared spectroscopic techniques for the non-invasive detection of glucose concentrations in the blood of humans.

In the diagnosis and treatment of various conditions, it is important to measure the concentration of various constituents in the blood. For example, in the treatment of diabetes, the concentration of glucose in the blood must be measured on a periodic basis. For persons experiencing insulin-dependent or Type I diabetes, it is often necessary or desirable to measure blood glucose concentration several times each day. Obtaining accurate readings of cholesterol concentrations is important in the prevention of coronary artery disease. The measurement of the concentration of other blood analytes, such as bilirubin and alcohol, is also important for various diagnostic purposes.

The accurate measurement of concentrations of such blood constituents, as it is now practiced, requires obtaining a blood sample, such as by pricking a finger. The obtaining of blood samples by such invasive techniques is both painful and inconvenient. In the case of diabetics, the need to lance a finger several times a day to monitor glucose levels results in a build-up of substantial scar tissue. Indeed, many diabetics are believed not to monitor their glucose level as frequently as recommended because of the pain and inconvenience of the invasive method. The result of such a failure to monitor glucose levels is a greater risk of experiencing the long-term health effects of diabetes. These health effects include damage to the eyes, resulting in partial and often total loss of vision, and damage to the extremities, which can result in the need to amputate. Millions of individuals in the United States alone suffer from diabetes. As a result, the failure of individuals afflicted with diabetes reliably to monitor their glucose levels is a significant public health problem.

In order to provide an alternative to the existing invasive blood glucose monitoring techniques, various non-invasive blood glucose detection techniques have been proposed. One of the most promising of these techniques is the non-invasive infrared spectroscopic technique. In this technique, a portion of the patient's skin is irradiated with infrared or near-infrared radiation. The resulting radiation that is either back-scattered or transmitted through a body part such as the finger, is then measured. By appropriate spectroscopic analysis techniques, it has been hoped that the concentration of glucose in the blood can be determined.

The ability to determine accurately the concentration of analytes in mammals, such as glucose in the blood of a diabetic, is directly related to the signal-to-noise ratio in the radiation resulting from the interaction of the incident radiation with the patient's body. One way to increase the signal-to-noise ratio of the resulting radiation, and thereby improve the accuracy of the determination of glucose concentration, is to increase the intensity (i.e., brightness) of the incident radiation. However, increasing the intensity of the incident radiation also increases the heating effect resulting from absorption by water in the body of incident radiation. The heating effect causes discomfort to the patient and even involves a risk of burning the patient.

It is accordingly an object of this invention to overcome the disadvantages and drawbacks of the prior art and to provide for the precise effective non-invasive determination of the concentration of analytes in a mammal, and particularly glucose in the blood of a human patient.

It is a specific object of this invention to provide a method for accurately determining analyte concentration without burning the patient's body.

Further objects and advantages of this invention will become apparent from the detailed description of a preferred embodiment which follows.

SUMMARY OF THE INVENTION

The present invention is a method and an apparatus for non-invasive determination of the concentration of at least one analyte in a mammal. According to the invention, a portion of the body of the mammal is irradiated with incident radiation, where the incident radiation includes two or more distinct bands of continuous-wavelength incident radiation. The resulting radiation emitted from the portion of the body is sensed and a value for the concentration of the analyte is derived from the sensed resulting radiation.

BRIEF DESCRIPTION OF THE DRAWINGS

For a better understanding of this invention, both as to its organization and as to its method of operation, together with additional objects and advantages thereof, reference is made to the following description, taken in connection with the accompanying drawings, in which.

DETAILED DESCRIPTION OF A PREFERRED EMBODIMENT

Figure 1:
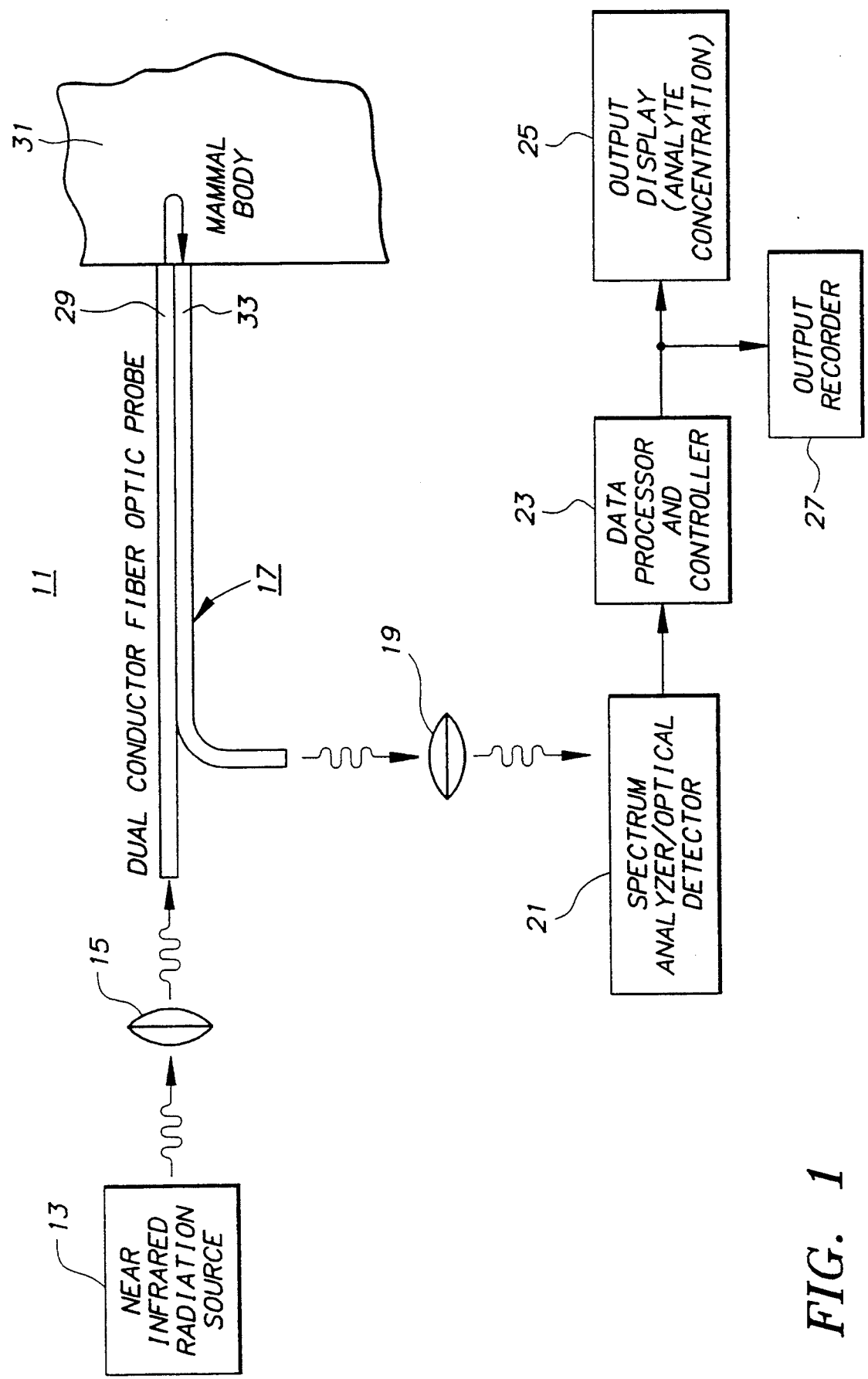
FIG. 1 is a block diagram showing an embodiment of this invention with which the method of invention is practiced.

FIG. 1 shows apparatus 11 for the non-invasive determination of the concentration of at least one analyte in a mammal. This apparatus includes a source 13 of near-infrared radiation, a first lens system 15, a dual conductor fiber-optic probe 17, a second lens system 19, a spectrum analyzer/detector 21, a data processor and controller 23, an output display device 25, and an output recorder 27.

Incident radiation from source 13 is focused by first lens system 15 onto fiber-optic probe 17, which transmits the incident radiation onto a portion 31 of the mammal's body. Probe 17 also receives and transmits resulting radiation from portion 31 to second lens system 19, which focuses the resulting radiation onto spectrum analyzer/detector 21. Spectrum analyzer/detector 21 analyzes the resulting radiation and data processor and controller 23 determines analyte concentration, which may be displayed on output display device 25 and/or recorded on output recorder 27.

Figure 2:
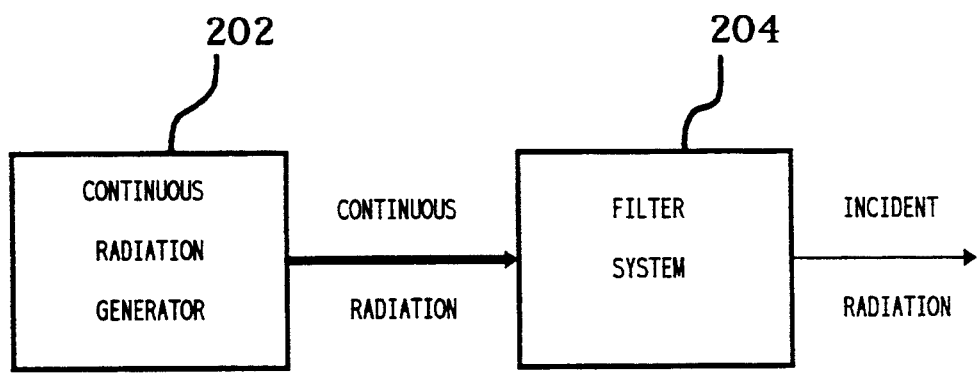
FIG. 2 is a block diagram of a preferred radiation source of the embodiment of FIG. 1.

Referring now to FIG. 2, there is shown a block diagram of radiation source 13 of FIG. 1 according to the present invention. Source 13 generates radiation that includes two or more distinct bands of continuous-wavelength radiation in the near-infrared range (i.e., between about 1300 nm and about 2400 nm). Radiation source 13 includes continuous-wavelength radiation generator 202 and filter system 204.

Continuous-wavelength radiation generator 202 may be a tungsten filament bulb. In order to maintain radiation intensity constant over time, the continuous-wavelength radiation generator 202 may be thermally isolated from its surroundings and the current through the filament may be maintained constant. Continuous-wavelength radiation generator 202 emits electromagnetic radiation across a continuous range of wavelengths. This continuous-wavelength radiation is transmitted from continuous-wavelength radiation generator 202 to filter system 204.

Filter system 204 filters the received continuous-wavelength radiation and transmits incident radiation. The incident radiation irradiates a portion of the body of a mammal. The incident radiation includes two or more distinct bands of continuous-wavelength radiation. That is, the incident radiation includes electromagnetic radiation in two or more distinct bands, each band having a continuous range of wavelengths.

Two bands of electromagnetic radiation are distinct if their respective continuous ranges of wavelengths do not overlap. For example, a first band having continuous radiation between band limits of 1650 nm and 1750 nm is distinct from a second band having continuous radiation between band limits of 1850 nm and 1950 nm, but the first band is not distinct from a third band having continuous radiation between band limits of 1700 nm and 1800 nm. Furthermore, radiation at a wavelength of 1790 nm, for example, may be said to "fall between" the first and second bands of continuous-wavelength radiation, because 1790 nm is greater than the wavelengths of the first band and less than the wavelengths of the second band.

For purposes of this specification, a band of radiation is considered continuous, (1) if the band contains all wavelengths between the band limits or (2) if, between the band limits, there are a sufficient number of discrete wavelengths that are separated by sufficiently small increments to permit pretreatment as described in further detail later in this specification. Thus, a band of continuous radiation may be generated by a single source (such as a single tungsten lamp) or by multiple sources (such as an appropriate set of infrared emitting diodes).

In a preferred embodiment, continuous-wavelength radiation generator 202 is a 35-watt tungsten filament bulb that generates radiation ranging from about 300 nm to about 3000 nm when operated at 9.7 watts. Filter system 204 preferably filters all radiation in the received continuous-wavelength radiation having wavelengths less than about 1300 nm and greater than about 2400 nm. Those skilled in the art will also understand that the term "filter" as used in this specification refers to any appropriate device that either blocks or attenuates electromagnetic radiation in specified wavelength ranges.

In addition to filtering wavelengths less than about 1300 nm and greater than about 2400 nm, filter system 204 filters radiation in one or more selected wavelength ranges within the 1300 nm to 2400 nm range, thereby defining two or more distinct bands of continuous-wavelength radiation. It is preferred that the selected wavelength ranges correspond to peaks in the spectrum of radiation absorption by water. The absorption of radiation by water in the body is believed to be a primary source of heating of the body during conventional methods of non-invasive determination of analyte concentration in mammals. Thus, by filtering radiation corresponding to water-absorption according to the present invention, the risk of burning the mammal is reduced.

By filtering radiation around the water-absorption peaks, the heating effect can be reduced with least reduction of data points. For example, by filtering out about 20% of the range from 1300 nm to 2400 nm, one may reduce the heating effect by about 70%.

In addition, because the water-absorption wavelengths are filtered, the intensity of the incident radiation at the transmitted wavelengths can be increased relative to the intensities employed in conventional non-invasive glucose determination methods. As a result, the signal-to-noise ratio and therefore the accuracy of the determination of analyte concentration are improved, without increasing the risk of burning the mammal.

Figure 3:
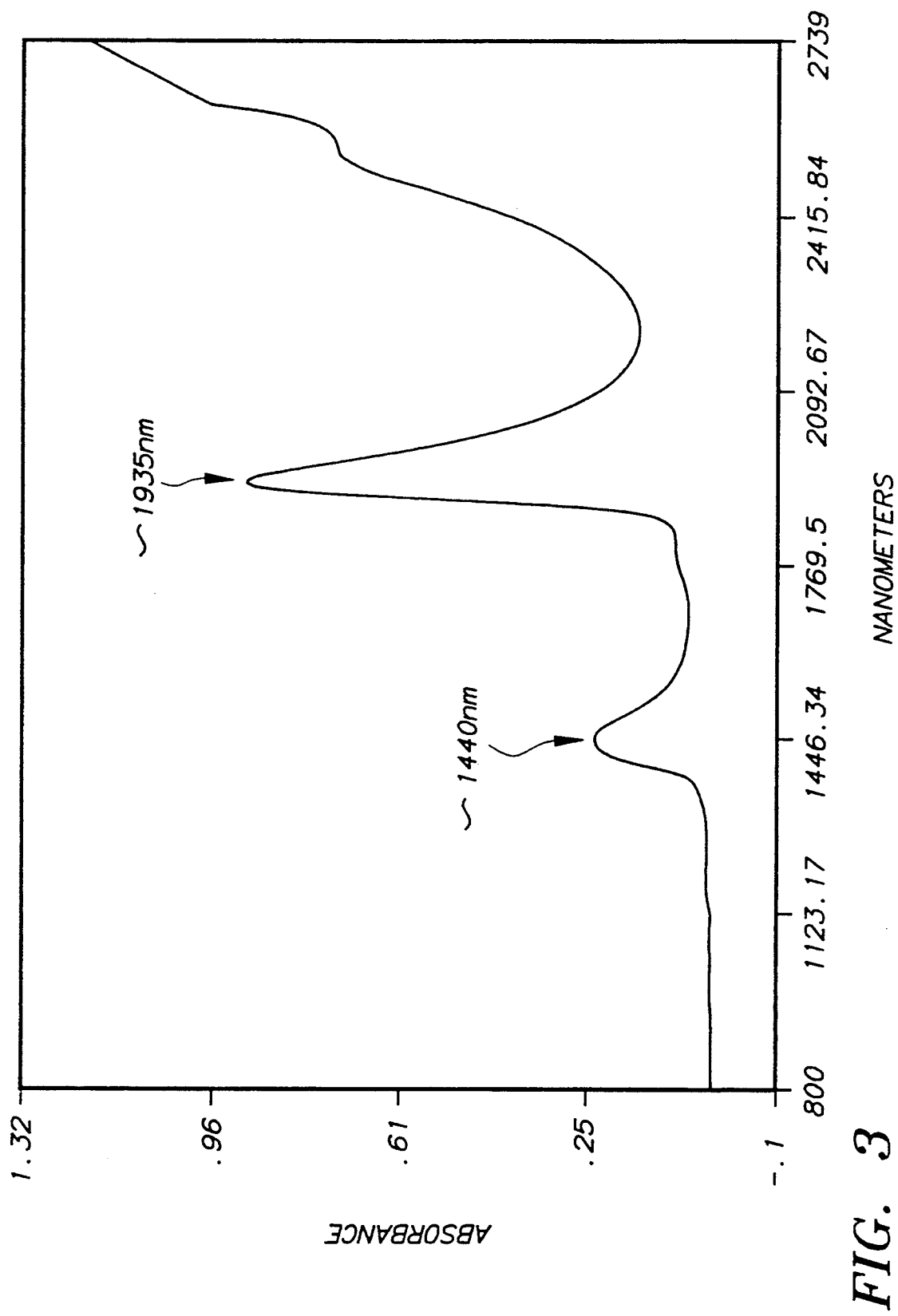
FIG. 3 depicts the absorbance spectrum of water in the near infrared wavelength range.
Figure 4:
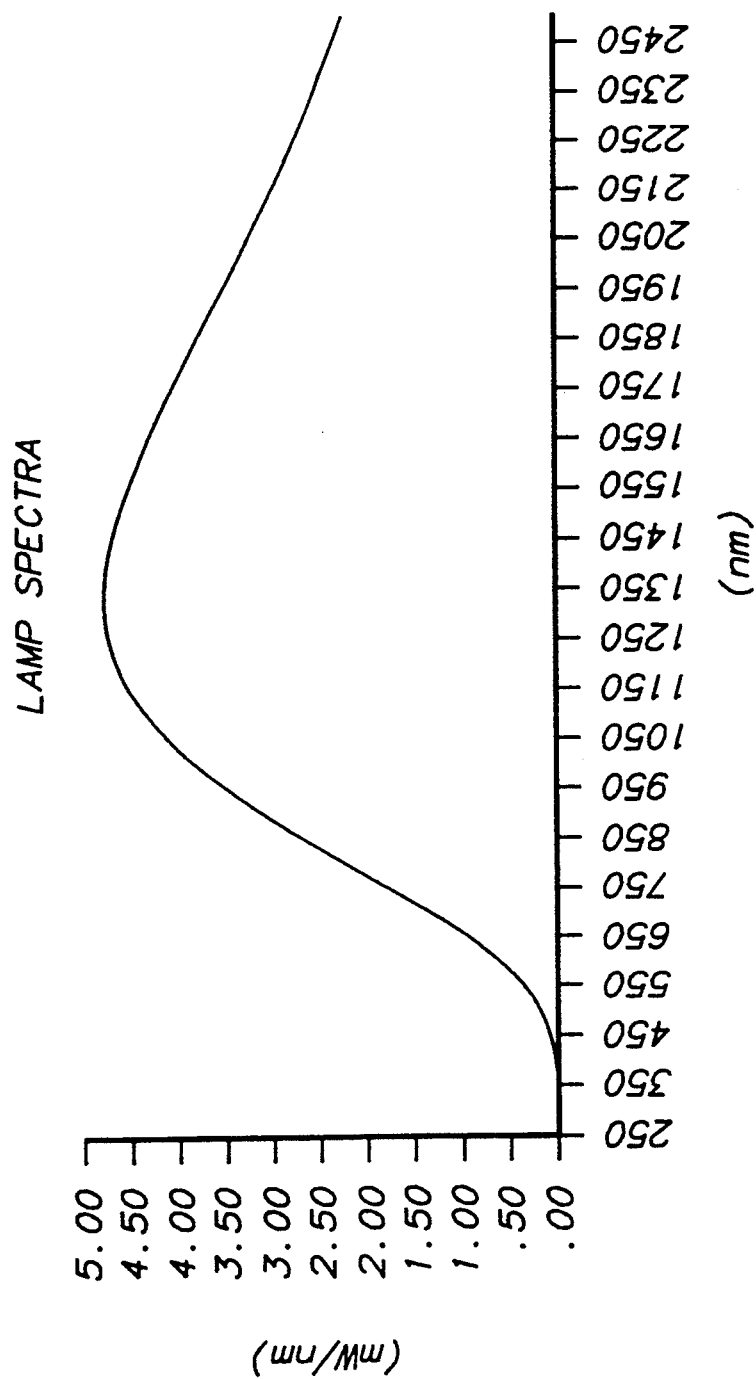
FIG. 4 depicts the continuous-wavelength radiation emitted by a continuous radiation generator of the radiation source of FIG. 2.
Figure 5:
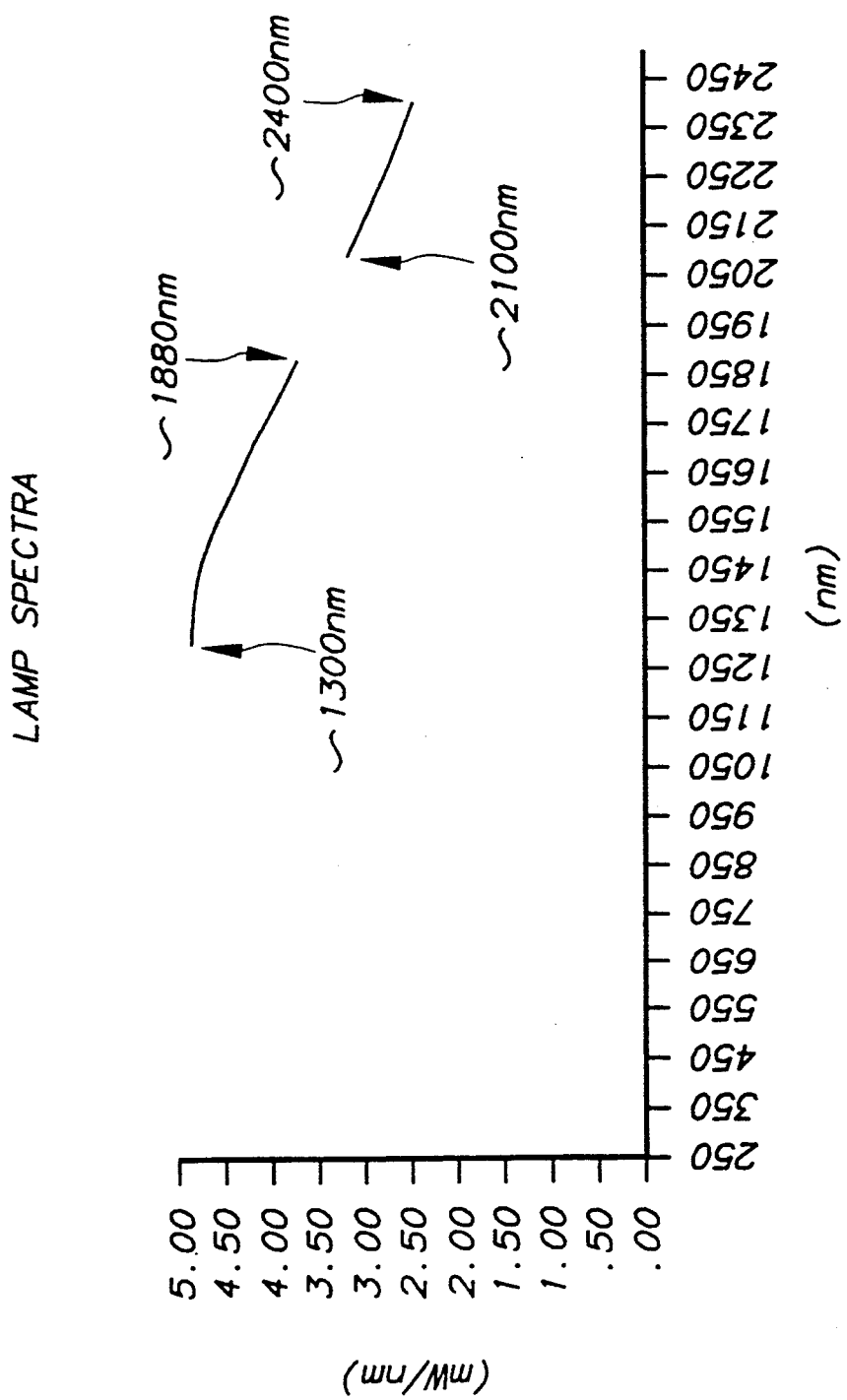
FIG. 5 depicts the incident radiation transmitted by the filter system of the radiation source of FIG. 2.

For example, as shown in FIG. 3, two peaks in the near-infrared absorption spectrum for water occur at about 1440 nm and 1935 nm. In a preferred embodiment of the present invention, filter system 204 filters radiation having wavelengths (a) less than 1300 nm, (b) between 1880 nm and 2100 nm, and (c) greater than 2400 nm. In this preferred embodiment, filter system 204 transmits incident radiation having two distinct bands of continuous-wavelength radiation: (i) from 1300 nm to 1880 nm and (ii) from 2100 nm to 2400 nm. FIG. 4 depicts the continuous-wavelength radiation emitted by continuous radiation generator 202 and FIG. 5 depicts the incident radiation transmitted by filter system 204.

Those skilled in the art will understand that filter system 204 may include combinations of appropriate wide-band interference filters and colored glass or dyed plastic to filter the continuous-wavelength radiation generated by continuous-wavelength radiation generator 202. The wide-band interference filters may be coatings applied to the glass or plastic components.

It will also be understood by those skilled in the art that radiation source 13 may be implemented using two or more different radiation sources with appropriate filtering to generate incident radiation according to the present invention. For example, two or more sets of infrared emitting diodes may be used to generate incident radiation having two or more distinct bands of continuous-wavelength radiation.

Referring again to FIG. 1, the lens systems 15 and 19 are represented by single-lens symbols. In actual practice, they are appropriate combinations of lenses including focusing lenses and collimators on the outlet side. Lens system 19 may include a spectrometer in a Czerny-Turner configuration. The fiber-optic probe 17 includes an input radiation conductor 29 for transmitting radiation to a portion 31, for example, an ear lobe or wrist, of the patient's body and pickup or sensing radiation conductor 33 for receiving the resulting radiation from the portion 31. The output end of the input conductor 29 and the input or sensing end of the pickup conductor 33 are preferably in firm contact with the outer surface of the portion 31 of the subject's body. While each conductor 29 and 33 is represented by a symbol for a single conductor, each radiation conductor, in actual practice of this invention, includes bundles of optical fibers.

Radiation from the source 13 is directed by the lens system 15 into conductor 29 and, at its outlet, is projected into the portion 31. This incident radiation induces scattered radiation within the body portion 31, some of which passes through the end of conductor 33 and through the conductor and is directed by lens system 19 into spectrum analyzer/detector 21. Spectrum analyzer/detector 21 may be a Model 6500 System Near Infrared Spectrometer acquired from Pacific Scientific Instrument Division, Pacific Scientific, Ltd., 2431 Linden Lane, Silver Spring, Md. 20910.

While FIG. 1 discloses apparatus in which scattered radiation is analyzed, the analysis of transmitted radiation, i.e., the input radiation less the back scattered and absorbed radiation, plus any forward scattered radiation, is within the scope of equivalents of this invention. In this case, the ends of conductors 29 and 33, instead of being side-by-side in contact with adjacent surfaces of the body portion 31, would be in contact with the outer surfaces on opposite sides of the body portion 31, for example, with opposite surfaces of the ear lobe. The radiation, which is in this case passed through conductor 33, is predominantly the radiation from the source 13 less the radiation scattered and absorbed by the molecules of the water in the blood, the glucose and other constituents of the blood. The skin also contributes to the scattering and absorption.

With the apparatus as shown in FIG. 1, the resulting back scattered radiation emitted by the body portion 31 is passed by pickup conductor 33 and lens system 19 to the spectrum analyzer/detector 21 where this radiation is spread into a spectrum. The spectrum is focused on an array of optical detectors. A selected wavelength range is focused on each detector. For example, a range of 15 nanometers may be focused on each detector. The detectors may be lead-sulfide detectors, which are well-known in the field of infrared spectroscopy of grains and other agricultural products. Each detector converts the radiation in the corresponding selected wavelength range to electrical signals which are transmitted to the data processor 23. In a preferred embodiment, intermediate each detector and the data processor, there is a pre-amplifier, an amplifier, and an analog-to-digital converter. It should be noted that, to reduce noise effects, a chopper is preferably provided before the detector to modulate the infrared beam. The amplifier is a lock-in amplifier, so that only the portion of the signal containing data is transmitted to the analog-to-digital converter.

The data processor then applies a step of pretreatment to the function of the magnitude of the radiation intensity versus wavelength. The step of pretreatment has the effect of minimizing, or eliminating, the effects of detector offset and drift. In a preferred embodiment, the pretreatment step comprises taking the nth derivative, and in particular, the second derivative, of the intensity vs. wavelength function. Alternatively, the pretreatment step may comprise the steps of subtracting the mean of the whole spectrum from each data point in the spectrum and then dividing each data point by the standard deviation of the whole spectrum.

The pretreated data is then subject to multivariate analysis. The result of the step of multivariate analysis is a glucose concentration. Various techniques of multivariate analysis are known in the chemical arts. A preferred multivariate analysis technique is partial least squares (PLS). The technique of partial least squares is taught in, for example, Geladi & Kowalski, Partial Least Squares Regression: A Tutorial, Analytica Chimica Acta, 185 (1986) 1–17. Various commercial software packages are available for implementation of the partial least squares technique. Such software packages are sold, for example, by NIR Systems, of Silver Spring, Md., under the name NSAS, (together with certain equipment), and in the Spectra Calc, Lab-Calc, and GRAMS software packages of Galactic Industries, of Salem, N.H. Other techniques such as principal component regression, principal component analysis, and multiple regression analysis (also called multiple linear regression analysis or ordinary least squares analysis) may also be used. Those skilled in the art of constructing models using these techniques will be able to do so using appropriate commercial software packages. The techniques of multiple regression analysis would ordinarily be employed if the number of data points is relatively small.

The first step in using multivariate techniques is the development of a model. The model relates various values of pretreated transmittance and reflectance with respect to wavelength to analyte concentrations. In developing the model, the device of the invention is employed to take measurements of reflected or transmitted light intensity on a subject. Simultaneously, invasive, highly-accurate methods are used to determine analyte concentrations. This process is accomplished over a range of analyte concentrations for two sets of data. One of these sets of data is the calibration set, and the other set is a prediction set.

The intensity values of the calibration set are pretreated, and are used as input for the multivariate model-developing software, together with the invasively-measured analyte concentrations. The software calculates, in the PLS technique, an initial set of factors, which make up an initial model. The initial model is then employed to obtain an analyte concentration from the prediction set infrared intensity values. This predicted value is then compared to the invasively determined analyte concentration obtained simultaneously with the prediction set infrared intensity values. A person suitably skilled in the art of constructing PLS models then reviews and analyzes the factors of the initial model and makes appropriate adjustments to develop an improved model. The techniques employed by a person skilled in the art of constructing multivariate statistical models are set forth in, for example, in Mark, Principles and Practice of Spectroscopic Calibration (1992). After an acceptable model has been iteratively developed, the model is employed in analyzing real data to obtain analyte concentrations.

One possible application of the present invention is to determine the concentration of glucose in the blood of a mammal. Glucose occurs in non-negligible concentrations in mammal tissue (i.e., the living cells) as well as in mammal blood. In living cells, glucose is metabolized into glucose phosphate which has an absorbance spectrum very similar to that of glucose. Accordingly, glucose phosphate will, by instruments using present technology, be detected as glucose.

Moreover, the concentrations of glucose in the blood stream and in the cells may differ from one another and may vary over time. In particular, in persons suffering from diabetes, who are most likely to employ non-invasive glucose sensing techniques, it has been observed that there is little predictable relation between the concentration of glucose in blood and the concentration of glucose in tissue. As a result, conventional non-invasive glucose sensors are difficult to calibrate accurately.

According to a preferred embodiment of the present invention, a calibration procedure employing a blood-volume modulation technique is performed to provide accurate determination of the blood glucose concentration in mammals. The calibration procedure preferably employs the following steps:

(1) employ the present invention to determine non-invasively the glucose concentration in a blood-rich body part of the mammal by irradiating the blood-rich body part of the mammal and detecting the resulting radiation;

(2) employ the present invention to determine non-invasively the glucose concentration in a blood-poor body part of the mammal by irradiating the blood-poor body part of the mammal and detecting the resulting radiation;

(3) employ a conventional technique to determine invasively the glucose concentration in the blood; and (4) perform the multi-variate analysis of the present invention to process the absorbance spectra from the blood-rich and blood-poor body parts and the blood glucose concentration determined invasively, to generate a set of factors that provide, when multiplied by a given spectrum, the blood glucose concentration.

After calibration, a blood-volume modulation technique, whereby radiation measurements are taken from both blood-rich and blood-poor body parts, is then preferably employed to determine the blood glucose concentration in the mammal non-invasively.

It will be appreciated that there are considerable variations that can be accomplished in a method and apparatus of the invention without departing from its scope. As a result, although a preferred embodiment of a method and apparatus of the invention has been described above, it is emphasized that the invention is not limited to a preferred embodiment and there exist other alternative embodiments that are fully encompassed within the invention's scope, which is intended to be limited only by the scope of the appended claims.

What is claimed is:

1. A method for non-invasive determination of the concentration of at least one analyte in a mammal, comprising the steps of:
   (a) concurrently irradiating a portion of the body of the mammal with incident radiation, said incident radiation including two or more distinct bands of continuous-wavelength incident radiation;
   (b) sensing the resulting radiation emitted from said portion of the body; and
   (c) deriving from the sensed resulting radiation a value for the concentration of said analyte.

2. The method of claim 1, wherein step (a) comprises the steps of:
   (1) generating continuous-wavelength source radiation; and
   (2) filtering said continuous-wavelength source radiation to generate said two or more distinct bands of continuous-wavelength incident radiation.

3. The method of claim 2, wherein said step of filtering decreases the intensity of said incident radiation relative to the intensity of said source radiation in a selected range of wavelengths intermediate a first and a second of said distinct bands and corresponding to a peak in the spectrum of radiation absorption by water.

4. The method of claim 1, wherein said incident radiation comprises near infrared radiation.

5. The method of claim 1, wherein radiation corresponding to a peak in the spectrum of radiation absorption by water falls outside of said two or more distinct bands of continuous-wavelength incident radiation.

6. The method of claim 1, wherein step (c) comprises the steps of:
   (1) deriving from the sensed resulting radiation a first expression for the magnitude of said sensed radiation as a function of wavelength of the sensed radiation;
   (2) pretreating said first expression to minimize the influence of instrument offset and drift to obtain a second expression for the magnitude of said sensed radiation as a function of wavelength; and
   (3) performing multivariate analysis of said second expression to obtain a value for the concentration of said analyte.

7. The method of claim 6, wherein said step of pretreating said first expression comprises the step of obtaining the nth derivative of said first expression.

8. The method of claim 6, wherein said step (c)(3) comprises the step of using the technique of partial least squares.

9. The method of claim 6, wherein said step (c)(3) comprises the step of using the technique of principal component analysis.

10. The method of claim 1, wherein step (b) comprises the step of concurrently sensing the resulting radiation emitted from said portion of the body with a plurality of detectors, wherein the resulting radiation comprises a plurality of wavelengths.

11. An apparatus for non-invasive determination of the concentration of at least one analyte in a mammal, comprising:
   (a) means for concurrently irradiating a portion of the body of the mammal with incident radiation, said incident radiation including two or more distinct bands of continuous-wavelength incident radiation;
   (b) means for sensing the resulting radiation emitted from said portion of the body; and
   (c) means for deriving from the sensed resulting radiation a value for the concentration of said analyte.

12. The apparatus of claim 11, wherein said irradiating means comprises:
   (1) means for generating continuous-wavelength source radiation; and
   (2) means for filtering said continuous-wavelength source radiation to generate said two or more distinct bands of continuous-wavelength incident radiation.

13. The apparatus of claim 12, wherein said filtering means decreases the intensity of said incident radiation relative to the intensity of said source radiation in a selected range of wavelengths intermediate a first and a second of said distinct bands and corresponding to a peak in the spectrum of radiation absorption by water.

14. The apparatus of claim 11, wherein said incident radiation comprises near infrared radiation.

15. The apparatus of claim 11, wherein radiation corresponding to a peak in the spectrum of radiation absorption by water falls outside of said two or more distinct bands of continuous-wavelength incident radiation.

16. The apparatus of claim 11, wherein said deriving means comprises:
   (1) means for deriving from the sensed resulting radiation a first expression for the magnitude of said sensed radiation as a function of wavelength of the sensed radiation; and
   (2) data processing means adapted to (i) pretreat said first expression to minimize the influence of instrument offset and drift to obtain a second expression for the magnitude of said sensed radiation as a function of wavelength and (ii) perform multivariate analysis of said second expression to obtain a value for the concentration of said analyte.

17. The apparatus of claim 16, wherein said data processing means is adapted to pretreat said first expression by obtaining the nth derivative of said first expression.

18. The apparatus of claim 16, wherein said data processing means is adapted to perform multivariate analysis of said second expression using the technique of partial least squares.

19. The apparatus of claim 16, wherein said data processing means is adapted to perform multivariate analysis of said second expression using the technique of principal component analysis.

20. The apparatus of claim 11, wherein said means for sensing the resulting radiation emitted from said portion of the body comprises a plurality of detectors for concurrently sensing radiation at a plurality of wavelengths.

* * * * *